United States Patent
Katz et al.

(10) Patent No.: US 7,403,815 B2
(45) Date of Patent: Jul. 22, 2008

(54) BRAIN STATE RECOGNITION SYSTEM

(75) Inventors: Bruce F Katz, Haverford, PA (US); Allon Guez, Penn Valley, PA (US)

(73) Assignee: Drexel University, Philadelphia, PA (US)

( * ) Notice: Subject to any disclaimer, the term of this patent is extended or adjusted under 35 U.S.C. 154(b) by 59 days.

(21) Appl. No.: 11/145,612

(22) Filed: Jun. 6, 2005

(65) Prior Publication Data
US 2005/0277813 A1 Dec. 15, 2005

Related U.S. Application Data

(60) Provisional application No. 60/577,463, filed on Jun. 4, 2004.

(51) Int. Cl.
*A61B 5/05* (2006.01)
(52) U.S. Cl. .................................................... 600/544
(58) Field of Classification Search ........................ None
See application file for complete search history.

(56) References Cited

U.S. PATENT DOCUMENTS

| 5,447,166 | A | * | 9/1995 | Gevins | 600/544 |
| 6,167,298 | A | * | 12/2000 | Levin | 600/545 |
| 7,024,238 | B2 | * | 4/2006 | Bergethon | 600/544 |
| 2003/0176806 | A1 | * | 9/2003 | Pineda et al. | 600/544 |

* cited by examiner

*Primary Examiner*—Robert L Nasser
(74) *Attorney, Agent, or Firm*—WolfBlock LLP

(57) ABSTRACT

An apparatus for assessing the brain state of a patient comprises at least one sensor to monitor at least one physiological variable, which provides at least one output signal. In addition, the apparatus for assessing the brain state of a patient comprises a computer processor for receiving the at least one output signal, wherein the computer processor filters the at least one output signal and applies pattern recognition techniques in evaluating the brain state of the subject. The computer processor comprises a first filtering module, which removes transient events not indicative of a brain state, and a second filtering sub-module, which groups together multiple modalities on the basis of classification techniques and incorporates additional information regarding mental states.

17 Claims, 3 Drawing Sheets

BRAIN STATE RECOGNITION SYSTEM

CROSS-REFERENCE TO RELATED APPLICATIONS

The present application claims the benefit of U.S. Provisional Patent Application 60/577,463, filed Jun. 4, 2004, the entirety of which is incorporated by reference.

FIELD OF INVENTION

The present invention relates to methods and apparatuses for recognition of a brain state of a subject. More particularly, this invention relates to methods and apparatuses that include monitoring one or more physiological variables associated with the subject via multiple sensors, filtering the data, and applying pattern recognition techniques and technology in the qualitative assessment of a brain state of a subject.

BACKGROUND OF THE INVENTION

Generally, there are devices in the health care, scientific research and mental health fields related to general pattern recognition of brain signals and to the recognition of brain activity. For example, there are techniques and apparatuses that measure brain activity through invasive examination, such as deep computing techniques to organize and respond to data from implantable medical devices and invasive examination using implantable electrodes. There are also techniques and apparatuses that measure brain activity through non-invasive examination. For example, there are methods and apparatuses for examining brain function through detection of the size of a subject's pupil, as well as through detection of electrical signals via an electroencephalogram (EEG), an electomyogram (EMG) and/or through electro-oculograph (EOG) techniques. As another example, there are other methods and apparatuses for recording electromagnetic activity in the brain, selecting a target pattern of electromagnetic activity produced by the brain and analyzing the sample of electromagnetic activity of the brain to identify a portion which contains the target pattern. However, such apparatuses and techniques lack complex signal analysis necessary to extract data from multiple sources.

Accordingly, there is a need for an apparatus and for a method for monitoring one or more physiological variables associated with cognitive/affective brain states via multiple sensors, filtering the data to reduce the complexity of the data before applying the learning algorithms that correlate the data with examined brain state, and applying pattern recognition techniques and technology in recognizing a brain state of a subject.

SUMMARY

The present invention relates to methods and apparatuses for monitoring one or more physiological variables associated with cognitive and affective brain states, filtering the data to reduce the complexity of such data before applying the learning algorithms that correlate the data with examined brain state, and applying pattern recognition techniques and technology in recognizing a brain state of a subject, including but not limited to a human.

In accordance with one aspect of the present invention, an apparatus for assessing the brain state of a patient comprises at least one sensor to monitor at least one physiological variable, which provides at least one output signal. In addition, the apparatus for assessing the brain state of a patient comprises a first filtering module, which removes transient events not indicative of a brain state, and a second filtering sub-module, which groups together multiple modalities on the basis of classification techniques and incorporates additional information regarding mental states. Together, the first filtering module and second filtering sub-module allow for a more effective system and method for correlating particular brain states with mental states.

DETAILED DESCRIPTION OF THE INVENTION

The present invention relates to a pattern recognition system for affective and cognitive brain state determination via multimodality sensors. In particular, the present invention relates to methods and apparatuses for monitoring one or more physiological variables associated with cognitive and affective brain states, filtering the data to reduce the complexity of such data before applying the learning algorithms that correlate the data with examined brain state, and applying pattern recognition techniques and technology in recognizing a brain state of a subject, including but not limited to a human.

The determination of affective and other qualitative brain states via multiple sensors is an under-explored area that is addressed by the present invention. Among other things, the system, methods and apparatuses of the present invention can distinguish between relatively long term qualitative states, such as degrees of alertness, interest, sadness, happiness, including other emotional states. Moreover, the present invention can provide information on the switching between brain states, such as that which occurs in surprise, elation, and insight.

Figure 1:
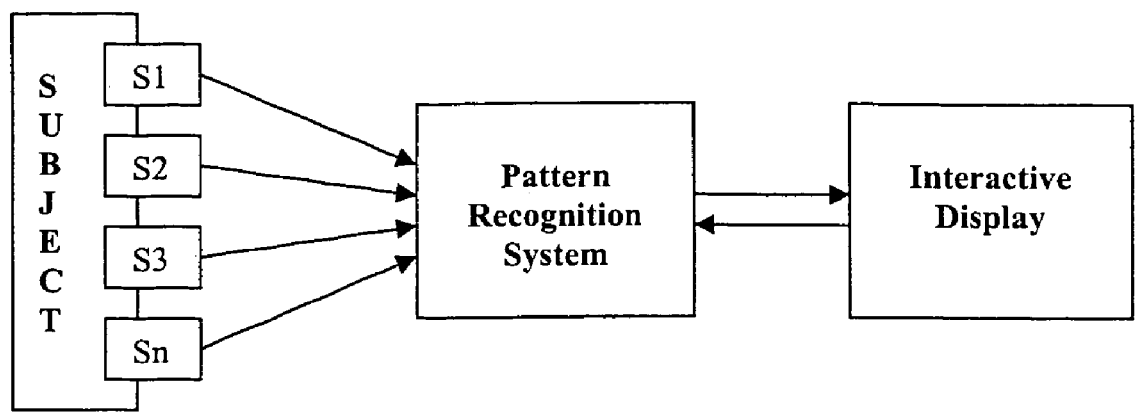
FIG. 1 is a schematic of a brain state recognition system according to an embodiment of the present invention.

In one embodiment of the present invention, the invention may accomplish the above-mentioned lists of tasks as illustrated in FIG. 1. A number of multi-modal sensors (S1, S2, S3, ... Sn) are connected to the human subject. These include but are not limited to electroencephalography (EEG), electromyography (EMG), near-infrared spectroscopy, or NIRS (a brain-imaging technique using near-infrared light that has shown promise in the noninvasive real-time determination of brain states), galvanic skin resistance (GSR) or any other technique or technology known in the relevant art. A pattern recognition system (center box) analyzes these signals for their correlation with known results, including the subjects' own real-time evaluation of the particular state under consideration, or for correlation with measures such as the success of an aesthetic experience as revealed by objective criteria (see the second embodiment, below). Results may be displayed on an interactive display or other analogous technology. Such a display would allow a technician to focus on interesting subsets of the multi-modal signal.

As illustrated in FIG. 1, the present invention relies on multi-modal signals, which permit, among other things, one modality to compensate for the weaknesses of other methods, ensuring the greatest possibility of detecting the desired affective or qualitative state.

Figure 2:
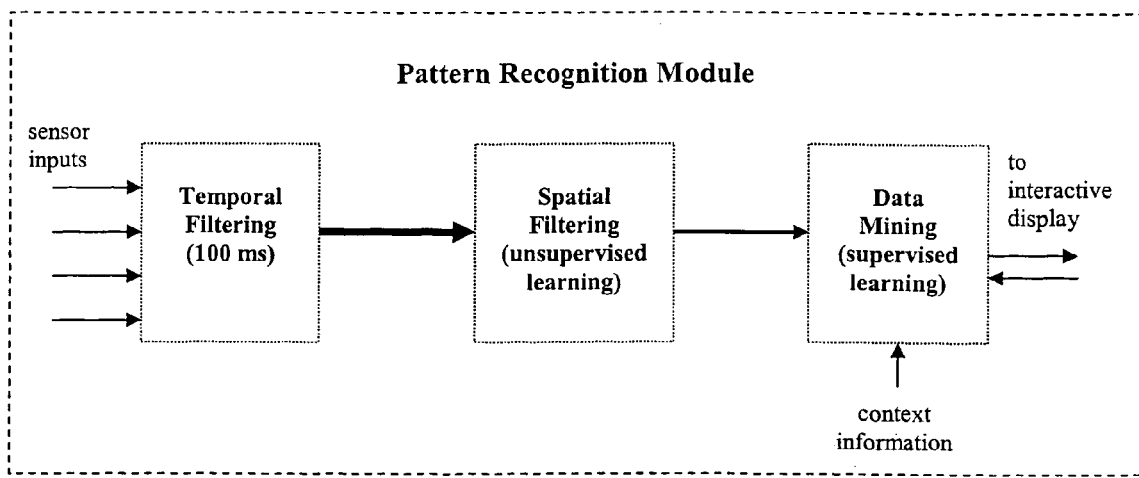
FIG. 2 is a schematic of a pattern recognition module for use with the brain state recognition system of FIG. 1 according to an embodiment of the present invention.

The Pattern Recognition module is illustrated in FIG. 2. The single largest problem that arises with a multi-sensor system is the sheer amount of information received from the sensors. Accordingly, another aspect of the present invention proposes using at least one filtering module that precedes the actual pattern recognition per se. A first filtering module grouping together events within approximately 100 ms windows removes transient short-lived events that are not indicative of stable attractors in the brain which are likely to correspond to mental states. This module and/or a second filtering sub-module then groups together separate aspects of a single modality or multiple modalities within the given temporal window on the basis of unsupervised classification techniques such as ISODATA and self-organizing maps (SOM). Together, this module effectively reduces an extremely large dimensional space to one that may tractably be used by yet another sub-module or pattern recognition module, which is responsible for the actual correlation between brain and mental states. This sub-module or pattern recognition module takes as input past contextual information regarding actual mental states, and using a variety of supervised learning techniques, mines the reduced dimensional sensor information to produce the desired correlations. Multi-input, multi-output pattern (MIMO) recognition techniques will be used at this stage, including non-linear regression, simulated annealing, genetic algorithms (GA), neural learning, statistical machine learning, and stochastic optimization techniques, or some combination of the above, as the case warrants.

In yet another embodiment of the present invention, the present invention may be used to aid in the diagnosis and prognosis of depressive disorders. Pathological depression will affect approximately 1 in 10 men and 1 in 4 women at some time in their lives, and has been called the "common cold of psychiatric illnesses." However, there still do not exist agreed upon means of evaluating the severity and time course of the illness through imaging techniques. Furthermore, it has been shown that the efficacy of pharmaceutical treatments is reflected in pre-frontal cortical activity before the treatment manifests itself in patient self-evaluations. The present invention, and in particular the combination of NIRS and EEG signals, can provide a quick and painless method of monitoring this efficacy so that alternative methods can be attempted before waiting for a treatment to have behavioral or phenomenological consequences.

In still another embodiment of the present invention, the present invention may be used to monitor brain activity during an aesthetic experience. For example, the real-time responses of a number of subjects can be monitored while viewing an advertisement, a movie, or a piece of music or any other medium that evokes emotion or brain activity. From a commercial point of view, success of these products depends on the experience containing some pleasurable reference point or so-called "hook", that is an emotionally charged or otherwise heightened moment that captures and entrances the mind. The present invention can be used to monitor both attentiveness and activity, the combination of which is indicative of this heightened state.

In yet another embodiment, the present invention may be used to monitor alertness as it correlates with performance on a given task. The neural and other physiological correlates of performance on a task, whether it be a video game, or one involving greater movement, can be monitored as these tasks are accomplished. One interesting, and still unsolved question is why there is such great variability in performance on a fixed task, especially as that task increases in difficulty. For example, on any given day, a golfer may hit a chip shot onto the green, place it firmly in the bunker, or miss the ball entirely. To the extent that it is possible to determine the correlates of this variability, it may be possible to provide the conditions that reduce the mental states that result in undesirable performance.

It is important to note that the present invention is not limited to these embodiments. In general, any transient dynamic state, can in principle be correlated with a cognitive or affective state of the brain. General pattern recognition techniques can be used to extract the maximum information from the information in the multiple signals to ensure that maximal predictability of these states can be extracted. Thus, the present invention may be thought of as a new window into the brain, one that is at once painless, dynamic, and most crucially, enables the determination of affective states, in some cases before the subject themselves is aware of these states.

The method and device of the present invention has multiple applications in a wide variety of fields, the applications including but not limited to the detection of depression and other affective disorders; the assessment of efficacy for treatments for depression and other affective disorders; the recognition of the brain's aesthetic evaluation for music, movies, and other similar works; the assessment of mental alertness and performance; the assessment of surprise, elation and the "aha" phenomena; and the assessment of insight and creativity.

Furthermore, the method and device of the present invention comprises multi-modal sensing to maximize information about brain states, temporal/spatial filtering to reduce unwanted information in sensor information, and novel sensory devices.

Accordingly, the goal of the current invention is the determination of relatively long term affective brain states, such as degrees of alertness, interest, sadness, happiness, and other emotional states, and in addition, the determination of states indicative of transitions between brain states, including but not limited to surprise, insight and elation. In order to accomplish this aim, a multi modality sensor system is proposed which comprises EEG, EMG, LAIRS, GSR, or other assessment techniques known in the relevant art. The data from these sensors will be fed into a pattern recognition system, which first filters the data in both the spatial and temporal domains in order to remove noise and to reduce the complexity of these inputs, and then calls upon a variety of correlation methods to determine the invariants of the aforementioned brain states.

Figure 3A:
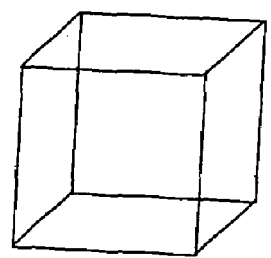
FIG. 3A is a perspective view of the visually ambiguous Necker cube corresponding to a brain state according to an embodiment of the present invention.

Referring again to the filtering mechanism depicted in FIG. 2, it is well-known that while the brain is a highly complex and dynamic system, it conforms to a large extent to a relatively regular sequencing pattern. In particular, one can conceive of this large-dimensional system as moving from one steady-state, or attractor, to the next, with the times spent in the steady states indicative of the underlying cognitive or affective state. For example, when viewing the ambiguous Necker cube illustrated in FIG. 3A, the steady states will be the two views of the cube corresponding to the cases where the lower square is the front face, and the upper square is the front face. Each view will correspond to a relatively long-term and steady brain state, with the transition between states occupying a relatively small amount of the total processing time.

Figure 3B:
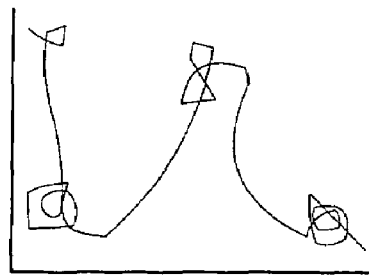
FIG. 3B is a graph representing trajectory of brain states according to an embodiment of the present invention.
Figure 3C:
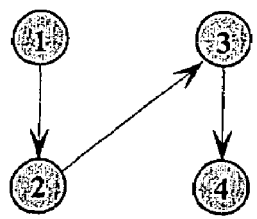
FIG. 3C is a flowchart of a finite state machine representing the successive brain states shown in FIG. 3B.

In general, we may conceive of the trajectory of brain states as in FIG. 3B. In this diagram, the attractors or long-term states of the system appear as knots, wherein the state of the brain remains relatively unchanged during this period. The transitions are the curves between the knots. The task of the filtering system will be to take a multi-dimensional counterpart to Figure B, containing the multi-modal sensor outputs, and convert it to the finite state machine shown in C. In this diagram, the successive states are represented by numbered circles, and the transitions by the arrows between these objects. The advantage of this method is that it presents the final task in the algorithm represented in FIG. 2, data mining, with a highly reduced set of data in order to make this process both more efficient and more accurate. Without such filtering, the data mining module would be presented with both a much larger number of variables, and in addition, would be forced to take into account the extra information generated during the state transitions. However, this information does not appear to be indicative of the cognitive/affective state of the person, and therefore may be ignored in the search for such states.

The nature of the mechanism to accomplish this filtering is as follows. Let $x_1(t), x_2(t), \ldots x_n(t)$ be a number of time-varying sensor signals or their transformed equivalents, for example, the Fourier transforms or suitable wavelet reductions of the original signals. The filter works by first detecting the existence of an attractor over these signals, and then rejecting the signals outside the duration of the attractor. Three primary types of attractors are possible. The first, or steady state attractor, is characterized by relatively little change as time proceeds. Thus, an indication that such an attractor has been reached is simply $$\|x_i'(t)\| < \epsilon, \quad (1)$$

where the $x_i'$ are the time derivatives of the sensor signals, $\epsilon$ is small number, and $\|.\|$ is the appropriate norm. The second type of attractor of interest is the so-called cyclic attractor. In this case, the signals are not static as in a fixed-point attractor. However, they do, by definition, return to a given point in the space of the variables in a periodic fashion. Thus, the previous indicator can be modified as follows:

$$\|X_i'(t)\| < \epsilon, \quad (2)$$

where the $X_i$ are the Fourier transformed $x_i$'s. In this case, instead of expecting the signals to hold steady, we assume that they will be periodically steady; this will be indicated by a frequency spectrum that is relatively invariant for a given time window. The final attractor of interest and the most complex is the so-called chaotic attractor. In this case, there is no guarantee of periodicity. However, such an attractor is characterized by the confinement of the signal variables to a relatively proscribed area of the space of possible values. If, for example, this region is a hypersphere, the characteristic condition for the attractor is $$\|x_i(t) - c_i\| < \rho, \quad (3)$$

where $c_i$ is the ith component of the center of the hypersphere and $\rho$ is radius of the chaotic attractor. Note that (3) is a considerably weaker condition than either (1) or (2) but still may be indicative of brain dynamics that correspond to an enduring cognitive or affective state.

The present invention stands in sharp contrast to existing methods in that a) it harnesses the information in multiple sensory modalities simultaneously, and b) calls upon a variety of unsupervised and supervised learning techniques to extract the maximum possible information from these signals. Thus, the present invention allows a number of novel applications including but not limited to long term affective evaluation, critical in the treatment of depression and other affective disorders, short term affective evaluation, to determine the reaction to a commercial work such as a movie or piece of music, and alertness assessment, crucial to determining performance on a physical or mental task.

Other cognitive and affective states of a human subject that may be indicated include, but are not limited to, i) the long-term affective state of subject (e.g., depressed or otherwise), ii) the affective response to a product, iii) the affective response in real-time to a product that changes in time such as a piece of music or a movie, iv) the degree to which there is a need for the product or the desire to purchase it, v) the alertness or lack thereof of the subject, vi) the degree of insight the subject is currently experiencing, vii) the degree to which the brain of the subject is or is not in a state of correlated with optimal performance on a physical or mental task, viii) other positive fleeting states such as but not limited to humor, elation, and comfort and other negative states such as but not limited to anxiety, nervousness, and fear.

While illustrated and described above with reference to certain specific embodiments, the present invention is nevertheless not intended to be limited to the details shown. Rather, the present invention is illustrative of a method and device for recognition of a brain state of a subject.

The invention claimed is:

1. An apparatus for assessing a brain state of a subject, the apparatus comprising:
   at least one sensor capable of monitoring at least one physiological variable and providing at least one output signal related to the at least one physiological variable, the output signal comprising temporal segments indicative of attractor states and temporal segments indicative of non-attractor states;
   a computer processor capable of receiving the at least one output signal and processing the said signal, said computer processor further capable of relating said signal to at least one brain state profile; and
   wherein the computer processor comprises a filtering module and a pattern recognition module, wherein the filtering module filters only the temporal segments indicative of attractor states from the output signal for processing.

2. The apparatus of claim 1, wherein the at least one sensor is a NIR sensor.

3. The apparatus of claim 1, further comprising a plurality of sensors, wherein the sensors are selected from the group consisting of EEG sensors, EMG sensors, NIR sensors, and GSR sensors.

4. The apparatus of claim 3, wherein the plurality of sensors comprises at least two different types of sensors.

5. The apparatus of claim 1 wherein the attractor states are selected from the group consisting of steady state attractors, cyclic attractors and a chaotic attractors.

6. An apparatus for assessing a brain state of a subject, the apparatus comprising:
   at least one sensor coupled to a subject capable of monitoring at least one physiological variable and providing at least one output signal related to the at least one physiological variable, the output signal comprising temporal segments indicative of attractor states and temporal segments indicative of non-attractor states; and
   a computer processor for receiving the at least one output signal, wherein the computer processor filters only the temporal segments indicative of attractor states from the output signal, and applies pattern recognition techniques in evaluating the brain state of the subject.

7. The apparatus of claim 6, wherein the at least one sensor is a NIR sensor.

8. The apparatus of claim 6, further comprising a plurality of sensors, wherein the sensors are selected from the group consisting of EEG sensors, EMG sensors, NIR sensors, and GSR sensors.

9. The apparatus of claim 8, wherein the plurality of sensors comprises at least two different types of sensors.

10. The apparatus of claim 6 wherein the attractor states are selected from the group consisting of steady state attractors, cyclic attractors and a chaotic attractors.

11. A method for obtaining information about a brain state, comprising the steps of:
provided a recording system for recording brain state activity of a subject as brain activity data;
comprising temporal segments indicative of attractor states and temporal segments indicative of non-attractor states;
filtering the brain activity data by first extracting out only that data indicative of temporal segments indicative of an attractor state, as a means of processing only the states of the brain selected from a group consisting of cognitive and affective states;
applying computer implemented learning techniques to refine the extracted data to be presented to a pattern recognition phase; and
applying pattern recognition techniques to the refined data to evaluate the brain state activity of said subject.

12. The method for obtaining information about a brain state of claim 11, wherein the step of applying pattern recognition techniques comprises use of computer implemented pattern recognition techniques on the extracted data that correlate the extracted data with a subject's cognitive and affective states as revealed by the subject's communication.

13. The method for obtaining information about a brain state of claim 11, wherein the brain state activity is selected from the group consisting of a long-term affective state of subject, an affective response to a product, an affective response in real-time to a product that changes in time such as a piece of music or a movie, the degree to which there is a need for the product or the desire to purchase it, the alertness or lack thereof of the subject, the degree of insight the subject is currently experiencing, the degree to which the brain of the subject is or is not in a state of correlated with optimal performance on a physical or mental task, humor, elation, comfort, anxiety, nervousness and fear.

14. The method of claim 11, wherein the step of providing a recording system for recording brain state activity of a subject comprises attaching a sensor to the subject, wherein the sensor is a NIR sensor.

15. The method of claim 11, wherein the step of providing a recording system for recording brain state activity of a subject comprises attaching a plurality of sensors to the subject, wherein the sensor is selected from the group consisting of EEG sensors, EMG sensors, NIR sensors, and GSR sensors.

16. The method of claim 15, wherein at least two different types of sensors are attached.

17. The method of claim 11 wherein the attractor states are selected from the group consisting of steady state attractors, cyclic attractors and a chaotic attractors.

\* \* \* \* \*